(12) United States Patent
Feldkamp et al.

(10) Patent No.: US 8,773,117 B2
(45) Date of Patent: *Jul. 8, 2014

(54) CONDUCTIVITY SENSOR

(71) Applicant: Kimberly-Clark Worldwide, Inc., Neenah, WI (US)

(72) Inventors: Joseph R. Feldkamp, Appleton, WI (US); Jeffrey Robert Heller, Neenah, WI (US); Douglas Glen Laudenslager, Firestone, CO (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/753,813

(22) Filed: Jan. 30, 2013

(65) Prior Publication Data

US 2013/0141116 A1 Jun. 6, 2013

Related U.S. Application Data

(62) Division of application No. 12/464,431, filed on May 12, 2009, now Pat. No. 8,384,378.

(60) Provisional application No. 61/156,269, filed on Feb. 27, 2009.

(51) Int. Cl.
*G01N 27/12* (2006.01)

(52) U.S. Cl.
USPC ........... 324/236; 324/652; 324/228; 324/722; 600/547

(58) Field of Classification Search
USPC ......................... 324/635, 236, 652
See application file for complete search history.

(56) References Cited

U.S. PATENT DOCUMENTS

| | | |
|---|---|---|
| 4,114,606 A | 9/1978 | Seylar |
| 4,433,693 A | 2/1984 | Hochstein |
| 4,639,669 A * | 1/1987 | Howard et al. ............ 324/239 |

(Continued)

FOREIGN PATENT DOCUMENTS

| | | |
|---|---|---|
| EP | 1264746 | 12/2002 |
| EP | 1611841 | 1/2006 |
| GB | 1320403 | 6/1973 |

OTHER PUBLICATIONS

International Search Report and Written Opinion from PCT/IB2010/050168 dated Aug. 25, 2010—10 pages.

(Continued)

*Primary Examiner* — Richard Isla Rodas
(74) *Attorney, Agent, or Firm* — Dority & Manning, P.A.

(57) ABSTRACT

A conductivity sensor is disclosed. The conductivity sensor includes an oscillator for providing an input signal and a reactive circuit having an induction coil, a capacitive element, and a resistive element connected in parallel. The induction coil is adapted to be placed adjacent to a specimen. The conductivity sensor further includes a control circuit for driving the reactive circuit to resonance when the induction coil is placed adjacent to the specimen. The reactive coil is configured to provide an output signal having a parameter representative of the conductivity of the specimen when the reactive circuit is at resonance. The induction coil may include a first conductive element that spirals outward to an external perimeter and a second conductive element operably connected to the first conductive element. The second conductive element spirals inward from the external perimeter staggered relative to the first conductive element.

9 Claims, 9 Drawing Sheets

(56) References Cited

U.S. PATENT DOCUMENTS

| | | | |
|---|---|---|---|
| 4,688,580 A | 8/1987 | Ko et al. | |
| 4,727,332 A * | 2/1988 | Bundy | 327/321 |
| 5,400,236 A | 3/1995 | Shimizu et al. | |
| 5,489,847 A * | 2/1996 | Nabeshima et al. | 324/318 |
| 5,608,417 A * | 3/1997 | de Vall | 343/895 |
| 5,722,997 A | 3/1998 | Nedungadi et al. | |
| 6,025,725 A * | 2/2000 | Gershenfeld et al. | 324/652 |
| 6,147,881 A | 11/2000 | Lau | |
| 6,407,546 B1 * | 6/2002 | Le et al. | 324/230 |
| 6,573,712 B2 * | 6/2003 | Arai | 324/238 |
| 6,670,808 B2 * | 12/2003 | Nath et al. | 324/230 |
| 6,815,958 B2 * | 11/2004 | Kesil et al. | 324/662 |
| 6,916,968 B2 | 7/2005 | Shapira et al. | |
| 7,352,176 B1 * | 4/2008 | Roach et al. | 324/240 |
| 7,581,308 B2 * | 9/2009 | Finn | 29/600 |
| 7,755,351 B2 * | 7/2010 | Brady | 324/240 |
| 7,830,140 B2 * | 11/2010 | Tralshawala et al. | 324/222 |
| 2005/0090753 A1 | 4/2005 | Goor et al. | |
| 2006/0005845 A1 | 1/2006 | Karr et al. | |
| 2006/0033500 A1 | 2/2006 | Wang et al. | |
| 2006/0142658 A1 | 6/2006 | Perkuhn et al. | |
| 2007/0069717 A1 * | 3/2007 | Cheung et al. | 324/158.1 |
| 2007/0108972 A1 | 5/2007 | Blew et al. | |
| 2008/0048786 A1 * | 2/2008 | Feldkamp et al. | 331/16 |
| 2008/0071168 A1 | 3/2008 | Gauglitz et al. | |
| 2008/0077042 A1 | 3/2008 | Feldkamp et al. | |
| 2008/0149366 A1 * | 6/2008 | Suzuki et al. | 174/250 |
| 2008/0278275 A1 * | 11/2008 | Fouquet et al. | 336/84 M |
| 2010/0219841 A1 | 9/2010 | Feldkamp et al. | |
| 2010/0222696 A1 | 9/2010 | Feldkamp et al. | |

OTHER PUBLICATIONS

Arnold, et al., "Frequency Effects in the Inductive Measurement of Electrical Conductivity", *Journal of Physics E: Scientific Instruments*, vol. 21, pp. 448-453, May 1888.

Arthur et al., "Measuring Short-Term Rates of Milk Synthesis in Breast-Feeding Mothers", *Quarterly Journal of Experimental Physiology*, vol. 74, 1989, pp. 419-428.

Esrick et al., "The Effect of Hyperthermia-Induced Tissue Conductivity Changes on Electrical Impedance Temperature Mapping", *Phys. Med. Biol.*, vol. 39, pp. 133-144, 1994.

Frank et al., "Right- and Left-arm Blood Pressure Discrepancies in Vascular Surgery Patients", *Anesthesiology*, vol. 75, pp. 457-463, Sep. 1991.

Fung et al., "Elastic Environment of the Capillary Bed", *Circulation Research*, vol. 19, p. 441, Aug. 1966.

Gabriel et al., "The Dielectric Properties of Biological Tissues" I. Literature Survey, *Phys. Med. Biol.*, vol. 41, pp. 2231-2248, Apr. 1996.

Guardo et al., "Contactless Measurement of Thoracic Conductivity Changes by Magnetic Induction", *Proceedings—19th International Conference—IEEE/EMBS*, Oct. 30-Nov. 2, 1997.

Haemmerich et al., "In vivo Electrical Conductivity of Hepatic Tumours", *Physiological Measurement*, vol. 24, pp. 251-260 (2003).

Harpen, "Distributed Self-Capacitance of Magnetic Resonance Surface Coils", *Physics in Medicine and Biology*, vol. 33, No. 9, pp. 1007-1016, 1988.

Harpen, "Influence of Skin Depth on NMR Coil Impedance Part II", *Physics in Medicine and Biology*, vol. 33, No. 5, May 1988.

Harrison et al., "Estimation of Body Composition: A New Approach Based on Electromagnetic Principles", *The American Journal of Clinical Nutrition*, vol. 35, May 1982, pp. 1176-1179.

Hart et al., "A Noninvasive Electromagnetic Conductivity Sensor for Biomedical Applications", *IEEE Transactions on Biomedical Engineering*, vol. 35, No. 12, Dec. 1988.

Jackson, *Classical Electrodynamics*, Magnetostatics, Faraday's Law, Quasi-Static Fields, John Wiley & Sons, 3rd Edition, pp. 180-181, 1999.

Jayasree et al., "Non-invasive Studies on Age Related Parameters Using a Blood Volume Pulse Sensor", *Measurement Science Review*, vol. 8, Section 2, No. 4, 2008, pp. 82-86.

Leiderman et al., "Coupling Between Elastic Strain and Interstitial Fluid Flow: Ramifications for Poroelastic Imaging", *Institute of Physics Publishing*, vol. 51, 2006, pp. 6291-6313.

Liu et al. "Surrounding Tissues Affect the Passive Mechanics of the Vessel Wall: Theory and Experiment", *American Journal of Physiology: Heart Circulation Physiology*, vol. 293, H3290-H3300, Sep. 14, 2007.

Netz et al., "Contactless Impedance Measurement by Magnetic Induction—a Possible Method for Investigation of Brain Impedance", *Physiological Measurement*, vol. 14, pp. 463-471, Nov. 1993.

Pfeifer, "Vascular Medicine of the Lower Extremities", *Medscape-American Diabetes Association's 59th Scientific Sessions*, Jun. 22, 1999.

Reimann, "Nuclear Magnetic Resonance Field Discriminator Using Digital Techniques", *Journal of applied Mathematics and Physics*, vol. 18, 1967.

Roby, A Comparison of Two Noninvasive Techniques to Measure total Body Lipid in Live Birds, *The Auk*, vol. 108, Jul. 1991, pp. 509-518.

Schnyders et al., "Noninvasive Simultaneous Determination of Conductivity and Permeability", *Applied Physics Letters*, vol. 75, No. 20, pp. 3213-3215, Nov. 15, 1999.

Stinstra et al., "Modeling the Passive Cardiac Electrical Conductivity During Ischemia", *Medical Biology Computing*, vol. 43, No. 6, pp. 776-782, Nov. 2005.

Stoy et al., "Dielectric Properties of Mammalian Tissues From 0.1 to 100 MHz: A Summary of Recent Data", Phys. Med. Biol., 1982, vol. 27. No. 4, 501-513.

\* cited by examiner

CONDUCTIVITY SENSOR

PRIORITY CLAIM

This application claims the benefit of priority of U.S. Provisional Patent Application Ser. No. 61/156,269 filed on Feb. 27, 2009 and U.S. patent application Ser. No. 12/464,431 filed on May 12, 2009, which are incorporated herein by reference for all purposes.

BACKGROUND

The use of conductivity measurements to analyze various characteristics of specimens such as human tissue specimens and geological specimens has been shown to yield many practical advantages. For example, conductivity measurements have been used to distinguish diseased tissue from healthy tissue. Both conventional electrode and induction coil methods have been used to perform conductivity measurements of various specimens.

Conventional electrodes for measuring conductivity apply an AC voltage to a specimen of interest. The current traveling through the specimen is measured and the conductivity is computed. In some cases, many electrodes are attached so that imaging of the specimen is made possible in circumstances where conductivity varies spatially through the specimen.

A disadvantage of conventional electrodes is that it requires direct electrical contact with the specimen of interest. This is particularly true for specimens having a surface that impedes the flow of current through the specimen. For example, the stratum corneum layer of the epidermis may impede the flow of current through a human tissue specimen, leading to variable conductivity measurements. Conventional electrodes may also exhibit electrode polarization, resulting in inaccurate conductivity measurements.

Induction coil methods and devices for measuring conductivity have used a wide variety of induction coil designs including solenoids or simple loop type coils consisting of a few turns of wire. These coils may probe the specimen at depths allowing interferences from portions of the specimen that distort the conductivity measurement. Many of these devices also involve the use of expensive instrumentation to measure coil related parameters such as complex impedance and use circuitry that permits the induction coil to deviate from resonance as the coil is placed adjacent to a specimen, making measurement of conductivity more difficult.

Therefore, a need currently exists for an induction coil conductivity sensor that overcomes these deficiencies. An induction coil conductivity sensor that probes a specimen at sufficient depths while avoiding unnecessary interferences from the specimen would be particularly beneficial. Additionally, an induction coil conductivity sensor that drives the sensor circuitry to resonance when the induction coil is placed adjacent to the specimen would also be particularly beneficial.

SUMMARY

In one aspect of the present invention, a conductivity sensor for measuring the conductivity of a specimen is provided. The conductivity sensor includes an oscillator configured to provide an input signal and a reactive circuit operatively connected to the oscillator. The reactive circuit has an induction coil, a capacitive element and a resistive element connected in parallel. The induction coil is configured to be placed adjacent to the specimen of interest. The conductivity sensor further includes a control circuit for driving the reactive circuit to resonance when the induction coil is placed adjacent to the specimen. The reactive circuit provides an output signal having a parameter indicative of the conductivity of the specimen when the reactive circuit is at resonance. In particular aspects of the present invention, the parameter of the output signal may be the admittance or the impedance of the reactive circuit.

In a variation of this particular aspect of the present invention, the control circuit drives the reactive circuit to resonance by controlling the oscillator to provide a frequency sweep input signal. The frequency sweep input signal causes the reactive circuit to pass through resonance. The control circuit may include a voltage peak hold circuit and/or current peak hold circuit configured to determine the peak output voltage or peak output current of the reactive circuit. The peak hold circuits may be used to determine the output of the reactive circuit when the reactive circuit passes through resonance.

In another variation of this particular aspect of the present invention, the control circuit drives the reactive circuit to resonance by using a phase-locked loop circuit configured to tune the reactive circuit to resonance when the induction coil is placed adjacent to the specimen. For instance, the phase-locked loop circuit may tune variable capacitive elements, such as varactor diodes, connected in the reactive circuit in order to drive the reactive circuit to resonance. The phase-locked loop circuit may include a phase comparator configured to determine the phase difference between a voltage output and a current output of the reactive circuit. The phase comparator may be further configured to provide a control signal to a controller such as a digital signal processor representative of a phase difference. The controller may be configured to control the capacitance of the variable capacitive element until the reactive circuit achieves resonance. In a variation of this particular aspect of the present invention, the phase-locked loop circuit may be configured to maintain resonance of the reactive circuit at a fixed input frequency of the input signal.

In still another variation of this particular aspect of the present invention, the control circuit drives the reactive circuit to resonance by directing the variable capacitive element of the reactive circuit to provide a capacitance sweep through a range of capacitance. The capacitance sweep causes the reactive circuit to pass through resonance. The control circuit may include a voltage peak hold circuit and/or current peak hold circuit configured to determine the peak output voltage or peak output current of the reactive circuit. The peak hold circuits may be used to determine the output of the reactive circuit when the reactive circuit passes through resonance. The reactive circuit may pass through resonance at a fixed input frequency of the input signal.

In another aspect of the present invention, a conductivity sensor having an induction coil adapted to be placed adjacent to a specimen is provided. The induction coil includes a first conductive element that spirals outward to an external perimeter and a second conductive element operably connected to the first conductive element. The second conductive element spirals inward from the external perimeter staggered relative to the first conductive element.

In a variation of this particular aspect of the present invention, the induction coil may be located on a circuit board having a first side and an opposing second side. The first conductive element may spiral outward to an external perimeter on the first side of the circuit board and the second conductive element may spiral inward from the external perimeter on the second side of the circuit board. The external perimeter may have an external diameter in the range of about 5 mm to 120 mm, such as about 10 mm to 80 mm, such as about 30 mm to 40 mm, such as about 35 mm, or about 38 mm, or any other diameter or range of diameters therebetween.

In another variation of this particular aspect of the present invention, the induction coil may have a circular shape, elongated shape, elliptical shape, rectangular shape, triangular shape, hemispherical shape, fructo-hemispherical shape, or any other shape.

In a further variation of this particular aspect of the present invention, the induction coil may have a surface adapted to match the contours of the specimen. For instance, the induction coil may have a concave surface, a convex surface, or a waved surface designed to match the contours of the specimen.

In still a further variation of this particular aspect of the present invention, the induction coil may include a protective coating on the induction coil. The protective coating may be an insulating polymer and may have a thickness in the range of about 0.05 mm to 1.2 mm, such as about 0.08 mm to 0.8 mm, such as about 0.1 mm, or about 0.2 mm, or about 0.5 mm to 1.0 mm, or any other thickness or range of thickness therebetween. The protective coating may be composed of a dielectric material having a dielectric constant of less than about 10, such as less than about 5.

In still a further variation of this particular aspect of the present invention, the conductivity sensor comprises a base unit and a modular induction coil cartridge adapted to engage the base unit. The modular induction coil cartridge is removable from the base unit so that a variety of different modular induction coil cartridges may be used with a single base unit.

A further aspect of the present invention is directed to a method for measuring the conductivity of a specimen. The method includes oscillating an input signal through a reactive circuit comprising an induction coil, a resistive element, and a capacitive element connected in parallel; placing the induction coil adjacent to the specimen; driving the reactive circuit to resonance; and measuring an output signal of the reactive circuit at resonance. The output signal has a parameter indicative of the conductivity of the specimen.

In a variation of this particular aspect of the present invention, the step of driving the reactive circuit to resonance includes sweeping the frequency of the input signal so that the reactive circuit passes through resonance. In another variation of this particular aspect of the present invention, the step of driving the reactive circuit to resonance includes tuning the capacitance of the capacitive element until the reactive circuit achieves resonance. In a further variation of this particular aspect of the present invention, the step of driving the reactive circuit to resonance includes sweeping the capacitance of the capacitive element so that the reactive circuit passes through resonance.

Still a further aspect of the present invention is directed to a conductivity sensor for continuously monitoring the conductivity of a specimen over a period of time. The conductivity sensor includes an induction coil for performing a conductivity measurement, a controller configured to direct the conductivity sensor to perform a series of conductivity measurements comprising a plurality of conductivity measurements taken over a period of time. The conductivity sensor also includes a housing. The housing may be adapted to maintain the conductivity sensor adjacent to the specimen while the series of conductivity measurements is being performed.

In variations of this particular aspect of the present invention, the conductivity sensor may include a database configured to store the series of conductivity measurements. In particular aspects, the conductivity sensor may include a communications device for communicating the series of conductivity measurements to a remote device. In still other particular aspects, the conductivity sensor may comprise an alert system for triggering an alert when a conductivity measurement of the plurality of conductivity measurements reaches a predetermined threshold.

In other variations of this particular aspect of the present invention, the housing of the conductivity sensor is adapted to be secured to an extremity of an individual. For example, the conductivity sensor may include a strap to secure the conductivity sensor to the extremity of the individual. In another particular aspect, the conductivity sensor may be secured to an individual by an adhesive material. In still other aspects, the conductivity sensor may be part of a medical sling used to support an extremity of an individual. In still other aspects, the conductivity sensor may be part of a garment or uniform worn by law enforcement or military personnel.

Still a further aspect of the present disclosure is directed to a platform unit for measuring the conductivity of an individual. The platform unit includes a base unit configured to support an individual standing on the platform unit and an induction coil for performing a conductivity measurement of a foot of the individual standing on the platform unit. The platform unit may include a visual display configured to display the conductivity measurement to the individual. In variations of this particular aspect, the platform unit may comprise a plurality of induction coils for performing a conductivity measurement of a foot of an individual standing on the platform unit.

These and other features, aspects and advantages of the present invention will become better understood with reference to the following description and appended claims. It is to be understood that different embodiments, as well as different presently preferred embodiments, of the present subject matter may include various combinations or configurations of presently disclosed features, steps, or elements, or their equivalents (including combinations of features, parts, or steps or configurations thereof not expressly shown in the figures or stated in the detailed description of such figures). Additional embodiments of the present subject matter, not necessarily expressed in the summarized section, may include and incorporate various combinations of aspects of features, components, or steps referenced in the summarized objects above, and/or other features, components, or steps as otherwise discussed in this application. Those of ordinary skill in the art will better appreciate the features and aspects of such embodiments, and others, upon review of the remainder of the specification.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which:

FIG. 7b depicts a plan view of the exemplary conductivity sensor illustrated in FIG. 7a.

DETAILED DESCRIPTION

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment, can be used with another embodiment to yield a still further embodiment. Thus, it is intended that the present invention covers such modifications and variations as come within the scope of the appended claims and their equivalents.

In general, the present disclosure is directed to a conductivity sensor that drives the sensor circuitry to resonance when the induction coil is placed adjacent to the specimen. The induction coil sensor may be configured to prevent probing a specimen at excessive depths so that interferences arising from various internal parts of the specimen are avoided.

In one particular aspect of the present disclosure, the conductivity sensor includes an oscillator providing an input signal to a reactive circuit. The reactive circuit includes an induction coil, a capacitive element, and a resistive element connected in parallel. The induction coil of the reactive circuit is adapted to be placed adjacent to a specimen to measure the conductivity of the specimen.

The impedance and admittance of induction coil is related to and varies with the conductivity of the specimen. In particular, an input signal oscillating through the induction coil generates a time-varying primary magnetic field. The time-varying primary magnetic field induces a corresponding time-varying electric field. When the induction coil is placed near a specimen having a conductance or conductivity, the electric field generated by the induction coil generates eddy currents in the specimen. The eddy currents in turn generate a secondary magnetic field opposite to the primary magnetic field generated by the induction coil. This secondary magnetic field causes the impedance and admittance of the induction coil to change based on the conductivity of the specimen. Thus, the conductivity of a specimen may be measured by determining the impedance or admittance of the induction coil placed adjacent to the specimen as will be discussed in more detail below.

Figure 1A:
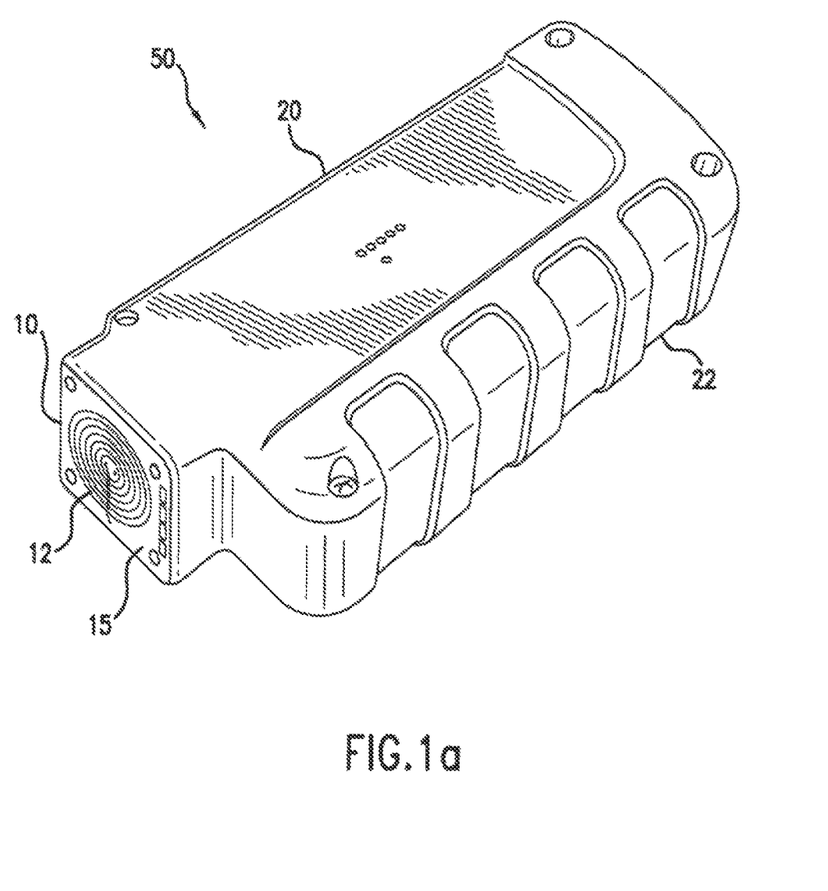
FIG. 1a depicts an exemplary embodiment of a conductivity sensor according to one embodiment of the present invention.

Referring now to FIG. 1a, an exemplary conductivity sensor 50 according to one exemplary embodiment of the present invention is illustrated. The conductivity sensor 50 has an induction coil 10 that is connected to a housing 20. Housing 20 may be any suitable housing for storing the circuitry and other components used to implement the conductivity sensor 50. For example, housing 20 may be a plastic housing that includes grooves 22 that facilitate gripping of the conductivity sensor 50. Using the teachings disclosed herein, those of ordinary skill in the art should appreciate that particular embodiments of the housing 20 are not meant as a limitation of the invention, and that embodiments of the present invention may encompass any configuration of features and functionality for storing and protecting circuitry and other elements and devices associated with the sensor 50.

Figure 1B:
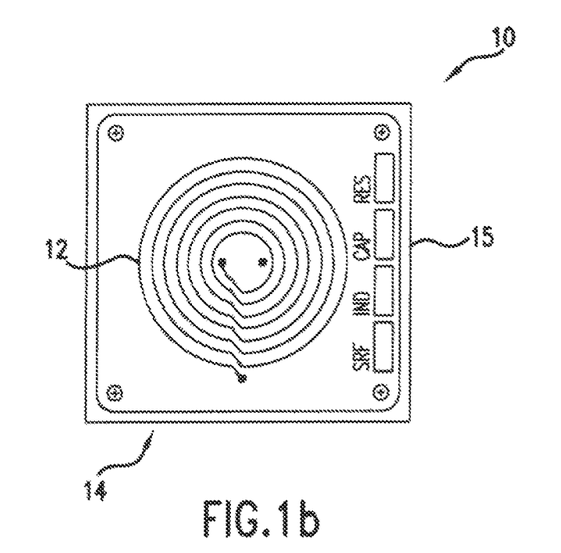
FIG. 1b depicts a plan view of an exemplary embodiment of an induction coil used in one embodiment of the present invention.

Referring now to FIG. 1b, an exemplary induction coil 10 according to one embodiment of the present invention is shown. The induction coil 10 includes a conductive element 12 disposed on a circuit board 15. Circuit board 15 may be a printed circuit board or any other board that is adapted or configured to mechanically support the conductive element 12. The circuit board 15 supports conductive element 12 on opposing first and second sides of the circuit board 15. First side 14 of circuit board 15 is illustrated in FIG. 1b.

Figure 1C:
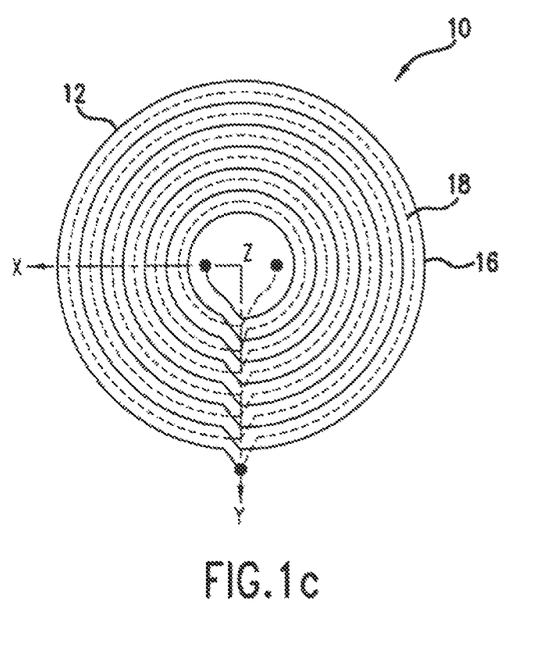
FIG. 1c depicts a plan view of an exemplary embodiment of an induction coil used in one embodiment of the present invention showing the second conductive element of induction coil spiraling inward staggered relative to the first conductive element.

As shown in FIG. 1c, conductive element 12 includes a first conductive element 16 spiraling outward on the first side 14 of the circuit board 15 and a second conductive element 18 spiraling inward on the second side of the circuit board 15. The second conductive element 18 spirals inward staggered relative to the first conductive element 16. In the embodiment shown in FIG. 1c, the first conductive element 16 spirals outward to an external diameter, passes to the other side of the circuit board 15, and then spirals inward as the second conductive element 18. The second conductive element 18 is staggered relative to the first conductive element 16. The external diameter of the induction coil 10 may be in the range of about 5 mm to 120 mm, such as about 10 mm to 80 mm, such as about 30 mm to 40 mm, such as about 35 mm, or about 38 mm, or any other diameter or range of diameters therebetween. The size of the induction coil is one factor that permits the induction coil to probe a specimen at sufficient depths while avoiding unnecessary interferences from the specimen, such as bone tissue or internal organs in human tissue specimens.

The induction coil 10 depicted in FIGS. 1a-1c is circular in shape. However, the induction coil 10 of the present invention may have a variety of shapes, sizes and configurations. For instance, the induction coil 10 may have an elongated shape, elliptical shape, rectangular shape, triangular shape, hemispherical shape, fructo-hemispherical shape or any other shape.

Figure 2:
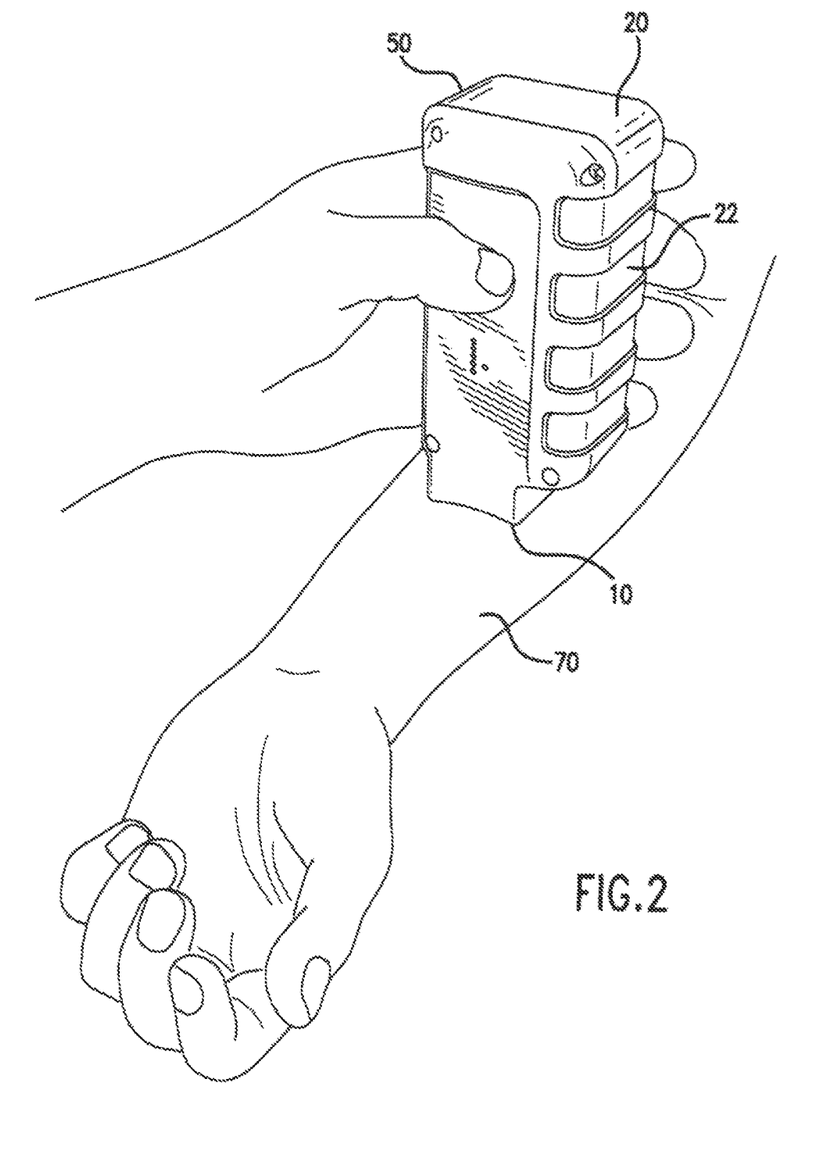
FIG. 2 depicts a perspective view of an exemplary conductivity sensor according to one embodiment of the present invention being placed adjacent to a person's forearm.

One embodiment of the induction coil 10 of the present invention may have a surface adapted to conform to the contours of a specimen. For instance, as illustrated in FIG. 2, the induction coil 10 may have a concave surface adapted to conform to the contours of a typical forearm 70. In other embodiments, the induction coil 10 may have a convex surface adapted to conform to the contours of a concave specimen. In still other embodiments, the induction coil 10 may have a waved surface to fit a specimen having waved contours.

An induction coil having a surface that conforms to the contours of the specimen can be more easily maintained a uniform distance from the specimen when performing conductivity measurements. Conductivity measurements are directly dependent on distance from the induction coil to the specimen. Thus, it is desirable to maintain the induction coil a specified or uniform distance from the specimen to ensure accurate conductivity measurements. Induction coils having a surface that conforms to the contours of the specimen allow for the induction coil to be maintained a more uniform distance from the specimen, leading to more accurate and repeatable conductivity measurements.

In other embodiments, the induction coil 10 may further include a protective coating on the outside of conductive element 12. The protective coating serves to protect the conductive element 12 of the induction coil 10 and to maintain the induction coil 10 a fixed distance from the specimen. For instance, an induction coil having a protective layer with a thickness of 0.07 mm can be maintained a uniform distance of 0.07 mm from the specimen. The protective coating may be any insulating polymer including, for example, polyurethane, polyesters, polyamides, polyvinyl chloride, polyolefins such as polyethylene and polypropylene, mixtures thereof, copolymers and terpolymers thereof, and other insulating polymers. The protective coating may also be formed of a dielectric material having a dielectric constant of less than about 10, such as less than about 5.

The thickness of the protective coating maintains a fixed, predefined distance between the induction coil 10 and the specimen. The thickness of the protective coating may be in the range of about 0.05 mm to 1.2 mm, such as about 0.08 mm to 0.8 mm, such as about 0.1 mm, or about 0.2 mm, or about 0.5 mm to 1.0 mm, or any other thickness or range of thickness therebetween. The predefined distance allows for consistency and repeatability when performing multiple conductivity measurements so that measurements can be compared or analyzed.

A protective coating on the induction coil 10 also allows for the induction coil 10 to be used repeatedly without hygienic concerns. For instance, if the induction coil 10 is used to measure the conductivity of human tissue specimens, the clinician or technician applying the induction coil 10 to the human tissue can simply wipe the induction coil clean using a disinfecting or other cleaning agent after each use.

To accommodate induction coils of varying shapes, sizes, and configurations, the conductivity sensor 50 may include a housing 20 having a base unit that is adapted to receive a modular induction coil cartridge that engages the base unit. The modular induction coil cartridge may be one of a plurality of modular induction coil cartridges with each modular induction coil cartridge having an induction coil with a different size, shape, protective coating, and/or configuration. A clinician or technician using the conductivity sensor will be able to substitute induction coils of varying sizes, shapes and configurations by simply disengaging one modular induction coil cartridge from the base unit and engaging a different modular induction coil cartridge with the base unit. In this manner, a variety of different induction coils may be used with a single base unit to provide for adaptability and flexibility of the induction coil sensor.

For example, a clinician or technician may be tasked with performing conductivity measurements of both a person's arm and leg. Instead of using the same induction coil to measure the conductivity of both the person's arm and leg, the clinician or technician may engage a first modular induction coil cartridge having an induction coil adapted to conform to the contours of the person's arm. After taking a conductivity measurement of the person's arm, the clinician may disengage the first modular induction coil cartridge and engage a second modular induction coil cartridge having an induction coil adapted to conform to the person's leg.

Figure 3:
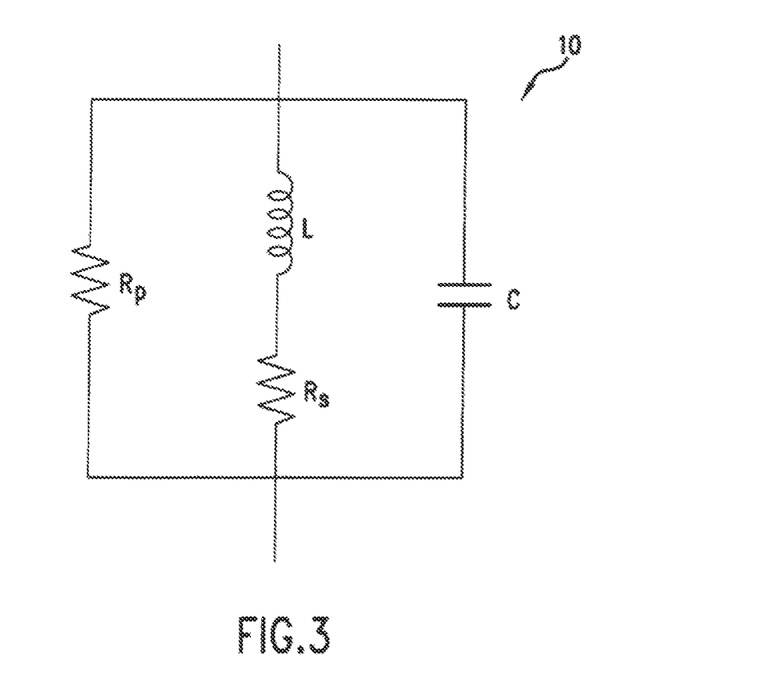
FIG. 3 depicts an equivalent circuit of an exemplary induction coil according to one embodiment of the present invention.

Referring now to FIG. 3, a model equivalent circuit of an exemplary induction coil 10 is provided in FIG. 2. As illustrated, the exemplary induction coil has an inductance L, inter-winding capacitance C, and coil resistances $R_p$ and $R_s$. The induction coil may include additional resistive elements and capacitive elements connected in parallel to form a reactive circuit. For instance, resistance $R_p$ may be supplemented with additional parallel resistive elements as shown in the exemplary reactive circuit depicted in FIG. 5. Similarly capacitance C may be supplemented with additional parallel capacitive elements in the form of, for instance, varactor diodes or other capacitive elements as shown in the exemplary reactive circuit depicted in FIG. 5.

The induction coil sensor according to certain embodiments of the present invention avoids probing the specimen at excessive depths so that interferences from portions of the specimen that may distort the conductivity measurement are avoided. For instance, if the conductivity sensor is used to measure the conductivity of human tissue, interferences arising from bone and other internal organs are avoided. Rather, the induction coil probes the soft tissue that is permeated by fine capillaries and relatively small arteries and veins. The probing depth of the induction sensor may be varied by altering the dimensions of the induction coil or by adjusting the resonant frequency of the induction coil reactive circuit.

For example, in one exemplary embodiment, the inductance of the induction coil may be in the range of about 3 to 4 microH, such as about 3.2 to 3.6 microH, such as about 3.4 microH, 3.5 microH, or any other inductance or range of inductance therebetween. The inter-winding capacitance of the induction coil may be about 10 pF. The self-resonance point of the induction coil would be approximately 27 MHz. In this particular embodiment, if additional parallel capacitance is added to adjust the resonant frequency to about 15 MHz, the electric field generated by the induction coil should penetrate to no more than a depth of approximately 15 mm, avoiding interferences from internal parts of the specimen, such as bone and internal organs in the case of human tissue specimens.

The operation of the induction coil conductivity sensor will now be discussed in greater detail. At resonance, the reactive circuit provides an output signal having a parameter that is indicative of the conductivity of the specimen. The parameter may be the impedance or admittance of the reactive circuit calculated from the voltage output and current output of the reactive circuit. The admittance of the reactive circuit is linearly proportional to the conductivity of the specimen when the reactive circuit is at resonance. The impedance of the reactive circuit is inversely proportional to the conductivity of the specimen when the reactive circuit is at resonance. The conductivity sensor uses these relationships to compute the conductivity of the probed specimen.

More particularly, the admittance and impedance of the reactive circuit at resonance are provided as follows:

$$A_{res} = \frac{1}{Z_{res}} \qquad (1)$$
$$= \frac{1}{R_P} + \frac{R_S}{R_S^2 + X_L^2}$$

where $X_L$ represents coil reactance. Resistance $R_s$ is equal to the sum of the coil resistance $R_L$ of the induction coil and the resistance $R_E$ originating in the eddy currents induced in the conductive specimen. If frequency is not too large $R_E$ varies linearly with specimen conductance σ, the square of angular frequency ω, and square of inductance L as follows:

$$R_E = \alpha' \sigma \omega^2 L^2 \qquad (2)$$

where α' is a frequency independent constant. Thus, when the reactive circuit with the induction coil is at resonance, the admittance of the reactive circuit is linearly proportional to the conductivity of the specimen and the impedance of the reactive circuit is inversely proportional to the conductivity of the specimen as follows:

$$A_{res} = \frac{1}{Z_{res}} \tag{3}$$
$$= \left(\frac{1}{R_P} + \frac{R_L}{\omega^2 L^2}\right) + \alpha' \sigma$$

According to this relationship, the reactive circuit admittance varies linearly with specimen conductivity, having a slope that is independent of frequency and an intercept that is nearly independent of frequency.

Because the above relationship applies only when the reactive circuit is at resonance, the conductivity sensor of the present invention includes a control circuit for driving the reactive circuit to resonance. A reactive circuit is at resonance when the reactance of the inductive elements is substantially equal to the reactance of the capacitive elements in the reactive circuit. At resonance, the phase angle between the current output and the voltage output of the reactive circuit is approximately 0 degrees, i.e. the current output and the voltage output are in phase. A reactive circuit can be driven to resonance by adjusting the frequency of the input signal oscillating through the reactive circuit or by tuning the capacitance or inductance of the capacitive and inductive elements in the reactive circuit.

After the induction coil is placed adjacent to a conductive specimen, the eddy currents generated in the conductive specimen cause the impedance of the induction coil to change. This change in impedance detunes the reactive circuit from resonance. The control circuit of the conductivity sensor drives the reactive circuit back to resonance so that the output signal of the reactive circuit is indicative of the conductivity of the specimen. For example, the control circuit may drive the circuit back to resonance by utilizing a frequency sweep input signal, phase-locked loop circuit, or capacitance sweep.

Figure 4:
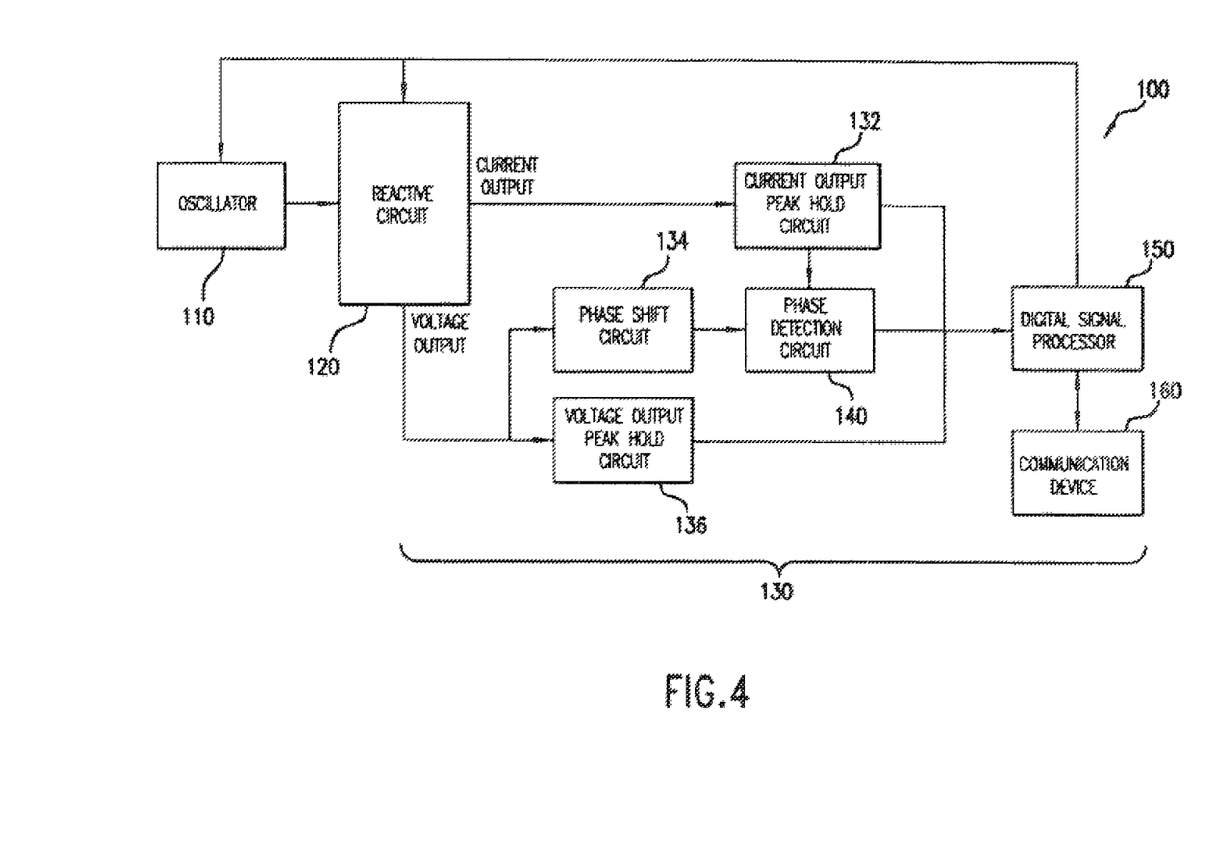
FIG. 4 depicts a block diagram of exemplary circuitry used to implement a conductivity sensor according to one embodiment of the present invention.

Referring now to FIG. 4, exemplary circuitry for a conductivity sensor according to one embodiment of the present invention will now be discussed in greater detail. FIG. 4 provides a block diagram of an exemplary conductivity sensor 100. The conductivity sensor includes an oscillator 110, reactive circuit 120 and control circuit 130. The electrical components or circuits of the conductivity sensor may be digital electronics, analog electronics or a combination of both. Those of ordinary skill in the art should appreciate that a variety of electronic devices and components may be used to perform the functions of the various components of the conductivity sensor and that the present invention is not limited to the use of any particular electronic or electrical components, devices, or circuits.

For example, oscillator 110 may be any device for generating an oscillating or alternating input signal for the reactive circuit. In one embodiment, the oscillator may be a function generator providing a stable constant voltage sine function to drive the reactive circuit. The oscillator 110 may be, for instance, the Analog Devices 9859 Direct Digital Synthesizer (DDS). Specifications for this oscillator include frequency adjustment from 10 to 20 MHz and a resolution of less than 10 Hz and an accuracy of 100 ppm. The oscillator 110 may include several filtering stages or a constant reference crystal. The frequency of the oscillator 110 may be adjusted by the control circuit 130. For example, the control circuit 130 may comprise a controller or digital signal processor 150 that controls the frequency of oscillator 110 via a SPI serial interface.

Figure 5:
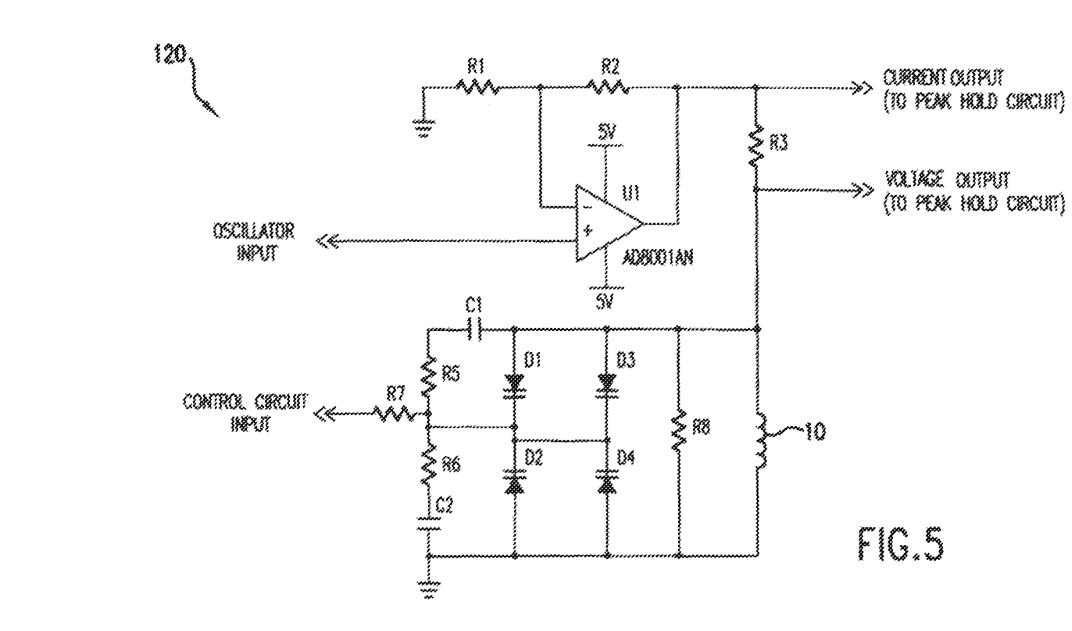
FIG. 5 depicts a circuit diagram of an exemplary reactive circuit according to one embodiment of the present invention.

Referring now to FIG. 5, an exemplary reactive circuit 120 comprising an induction coil 10 is illustrated. Exemplary reactive circuit 120 is driven by an input signal from the oscillator 110. Resistive elements R1 and R2 in conjunction with amplifier U1 make up a unity gain amplifier for impedance matching between the oscillator and the reactive circuit 120. For U1 to operate as a unitary gain amplifier, resistive elements R1 and R2 must have substantially equal resistance.

R3 is a sensing resistive element connected in series with a parallel RLC circuit having induction coil 10. Sensing resistive element R3 allows for current measurement through the reactive circuit and voltage measurement across the reactive circuit. In particular embodiments, the coil voltage may be directly measured, while coil current is calculated by digital signal processor 150 based on the value of R3. These voltage and current measurements operate as voltage and current output signals having parameters representative of the conductivity of a specimen when the reactive circuit is at resonance. For instance, the voltage output and current output may be used to calculate the impedance of the reactive circuit when the induction coil 10 is placed adjacent to a specimen.

As illustrated, induction coil 10 is connected in parallel with resistive element R8 and capacitive elements D1, D2, D3, and D4 to form a parallel RLC circuit. Resistive element R8 is added to the reactive circuit to reduce the Q factor of the reactive circuit. Q factor measures the degree of sharpness for a reactive RLC circuit. R8 may have a value of approximately 100 kΩ to make tuning the reactive circuit to resonance more achievable.

D1, D2, D3, and D4 are capacitive elements having an adjustable capacitance. In one embodiment, D1, D2, D3, and D4 are varactor diodes whose capacitance varies in proportion to the reverse bias voltage applied to the varactor diodes. R5, R6, C1, and C2 may be used to ensure that D1 and D3 strictly have a DC reverse bias. The control circuit 130 controls the capacitance of the varactor diodes D1, D2, D3, and D4 via a control signal. For instance, the control circuit 130 may comprise a controller 150 that controls the capacitance of the varactor diodes via a SPI serial interface and a digital to analog converter.

In operation, placing a conductive object in front of the coil 10 will cause an amplitude change in the voltage across the reactive circuit 120 and a phase shift between the voltage output and current output of the reactive circuit 120 indicating that the reactive circuit 120 is no longer at resonance. The control circuit 130 directs the reactive circuit back to resonance by either adjusting the frequency of the oscillator 110 or varying the capacitance of the varactor diodes D1, D2, D3, and D4 so that the output signal of the reactive circuit is accurately representative of the conductance of the specimen.

The exemplary control circuit 130 depicted in FIG. 4 comprises a current output peak hold circuit 132, phase shift circuit 134, voltage output peak hold circuit 136, phase detection circuit 140, and controller (digital signal processor) 150. The control circuit 130 is adapted to drive the reactive circuit 120 to resonance by controlling the oscillator to provide a frequency sweep signal, by using a phase-locked loop circuit to tune the capacitance of the reactive circuit, or by providing a capacitive sweep for the reactive circuit causing the reactive circuit to pass through resonance. Using the teachings disclosed herein, those of ordinary skill in the art should appreciate that a variety of circuit configurations and electrical devices may be used to drive the reactive circuit 120 to resonance and that the present invention is not limited to any particular circuit or electrical device.

For instance, current peak hold circuit 132 may be any device or circuit that receives as an input the current output of the reactive circuit 120 and allows for the measurement of the maximum current over a period of time. In one embodiment, the current peak hold circuit 132 may be Texas Instruments TLV3501 high speed voltage comparator which is configured to monitor and maintain maximum current. The output of the current peak hold circuit 132 may be sent to a controller 150 via, for instance, an analog to digital converter and a SPI interface. The time period over which the current output peak hold circuit 132 measures the maximum current may be controlled via the controller 150.

Voltage output peak hold circuit 136 may be any device or circuit that receives as an input the voltage output from the reactive circuit 120 and allows for the measurement of the maximum voltage over a period of time. For instance, the voltage output peak hold circuit 136 may be a Texas Instruments TLV3501 high speed voltage comparator which is configured to maintain the maximum voltage. The output of the voltage output peak hold circuit 136 may be sent to the controller 150 via, for instance, an analog to digital converter and a SPI interface. The time period over which the voltage output peak hold circuit 136 measures the maximum voltage may be controlled via the controller 150.

Phase detection circuit 140 may be any device or circuit that compares the phase of the current output of the reactive circuit 120 to the phase of the voltage output of the reactive circuit 120. The output of the phase detection circuit 140 indicates whether the reactive circuit 120 is at resonance. In particular, if the current output and the voltage output of the reactive circuit 120 are in phase, the reactive circuit 120 is at resonance. If the current output and the voltage output of the reactive circuit are not in phase, the reactive circuit 120 is no longer at resonance.

In one embodiment, phase detection circuit 140 may be Analog Devices AD8302 Phase/Gain comparator which provides a DC voltage output representing the phase difference of the voltage output and current output of the reactive circuit 120. The DC voltage output may be sent to the controller 150 via, for instance, an analog to digital converter and an SPI interface. If Analog Devices AD8302 is used as the phase detection circuit 140, the control circuit 130 should further include a 90 degree phase shift circuit 134 for shifting the voltage output of the reactive circuit 90 degrees. This is because the Analog Devices AD8302 Phase/Gain comparator may become non-linear if the current output and the voltage output of the reactive circuit 120 are exactly in phase, i.e. the reactive circuit 120 is at resonance.

The 90 degree phase shift circuit 134 may include a unity gain amplifier in an integrator configuration. However, those of ordinary skill in the art should recognize that any circuit for shifting the phase of the voltage output of the reactive circuit 120 by 90 degrees falls within the scope and spirit of the present invention. If a 90 degree phase shift circuit 134 is used, the phase detection circuit 140 will indicate that the reactive circuit 120 is exactly at resonance when the voltage input of the phase comparator 140 leads the current input of the phase detection circuit 140 by 90 degrees.

The controller 150 is the main processor or controller of the control circuit 130. The controller 150 accepts inputs from the current peak hold circuit 132, the voltage peak hold circuit 136, and the phase comparator 140. The controller 150 also includes outputs to control the frequency of the oscillator 110, and the capacitive elements of the reactive circuit 120.

The controller 150 may interact with one or more components to provide an indication of the measured conductivity of the specimen. For instance, the controller 150 may provide an output to a visual display for displaying the measured conductivity of the specimen. The controller 150 may also provide an output to an alarm system for providing a visual or audio alarm when the conductivity of the specimen reaches a certain threshold.

In addition, the controller 150 may interact with one or more communications devices 160 to interface with remote devices. For example, the controller may interact via a Bluetooth® wireless communication module to interface data collection and control application with a remote computer. The Bluetooth® wireless communication interface may be a Bluegiga WT12 Bluetooth® module that allows full duplex serial communications between the remote device and the controller 150. The controller 150 may also communicate via one or more communications networks. It should be appreciated that the communications device or medium can include one or more networks of various forms. For example, a network can include a dial-in network, a local area network (LAN), wide area network (WAN), public switched telephone network (PSTN), the Internet, intranet or other type(s) of networks. A network may include any number and/or combination of hard-wired, wireless, or other communication links.

The control circuit 130 may be adapted to drive the reactive circuit to resonance using a variety of electrical devices, circuits, control signals and techniques. In one embodiment, when the induction coil 10 is placed adjacent to a specimen, the control circuit 130 directs the oscillator 110 to provide a frequency sweep input signal. In this embodiment, the oscillator 110 sweeps the frequency of the input signal through a range of frequencies, including the resonant frequency of the reactive circuit 120. The control circuit 130 then determines the output signal of the reactive circuit 120 when the reactive circuit 120 passes through resonance. In one embodiment, the control circuit 130 may determine the resonant output signal of the reactive circuit 120 using the output of the current output peak hold circuit 132 and/or voltage output peak hold circuit 136. The output of the voltage output peak hold circuit 136 and/or the current output of the current output peak hold circuit 132 after the oscillator has performed a frequency sweep should be representative of the output signal of the reactive circuit 120 at resonance.

In another embodiment, the control circuit 130 includes a phase-lock loop circuit for tuning the reactive circuit 120 to resonance when the reactive circuit 120 is placed adjacent to a specimen. For instance, the phase-lock loop circuit for tuning the reactive circuit 120 to resonance may include phase detection circuit 140 and controller 150. Phase detection circuit 140 compares the voltage output signal of the reactive circuit 120 to the current output signal of reactive circuit 120 to determine if the voltage output signal and the current output signal are in phase (or leading by 90 degrees if a 90 degree phase shift circuit is used). If the voltage and current output signals are in phase, the reactive circuit 120 is at resonance.

If the impedance of the induction coil 10 changes when it is placed adjacent to a conductive specimen, resonance of the reactive circuit will be lost causing the voltage and current output signals to be out of phase. The phase detection circuit 140 provides a DC signal to controller 150 indicating the reactive circuit 120 is out of phase by a certain degree. The controller 150 then controls the variable capacitive elements to tune the reactive circuit 120 back to resonance. For instance, in one embodiment, the controller 150 may increase the reverse bias voltage across varactor diodes D1, D2, D3, and D4 to decrease the capacitance of the reactive circuit 120. Once the control circuit 130 has tuned the reactive circuit 120 to resonance, the phase locked-loop circuit ensures that the reactive circuit is maintained at resonance by adjusting the capacitance of the varactor diodes any time the reactive circuit 120 deviates from resonance.

In a variation of this particular embodiment, the phase-locked loop circuit may be configured to maintain the resonance of the reactive circuit 120 at a fixed input frequency provided by the input signal. In particular, the phase-locked loop circuit tunes the reactive circuit 120 to resonance by adjusting the capacitance of the capacitive elements of the reactive circuit 120 and does not vary the frequency of the input signal oscillating through the reactive circuit 120. Thus, the reactive circuit 120 achieves resonance at the fixed input frequency of the input signal.

By ensuring that resonance occurs at a fixed frequency, conductivity measurements are more predictable and repeatable. This is because the intercept of the linear relationship between admittance of the reactive circuit 120 and conductivity of the specimen is slightly dependent on the frequency of the reactive circuit. By maintaining the reactive circuit 120 at a fixed frequency, the linear relationship between the admittance and the conductivity of the specimen can be more effectively utilized. In addition, a conductivity sensor that achieves resonance at a fixed frequency avoids complex electronic circuitry associated with providing a variable frequency input signal. As a result, the circuitry supporting the conductivity sensor is more stable and has less electronic drift and noise.

In another embodiment of the present invention, the control circuit 130 may drive the reactive circuit 120 to resonance by controlling the variable capacitive element of the reactive circuit 120 to provide a capacitance sweep through a range of capacitance. For example, the controller 150 may control the reverse bias voltage across varactor diodes D1, D2, D3, and D4 so as to provide a capacitance sweep through a range of capacitance. The control circuit 130 then determines the output signal of the reactive circuit when the reactive circuit passes through resonance. In one embodiment, the control circuit 130 may determine the resonant output signal of the reactive circuit 120 using the output of the current output peak hold circuit 132 or voltage output peak hold circuit 136. The output of the voltage output peak hold circuit 136 and/or the current output of the current output peak hold circuit 132 after the capacitance sweep should be representative of the output signal of the reactive circuit 120 at resonance.

Similar with the phase-locked loop circuit, a controller 150 that is configured to provide a capacitance sweep to drive the reactive circuit 120 to resonance allows the reactive circuit 120 to pass through resonance at a fixed input frequency. As set forth above, this has various advantages including more predictable and accurate conductivity measurements as well as more simplified and stable electronic circuitry with less electronic drift and noise.

Figure 6:
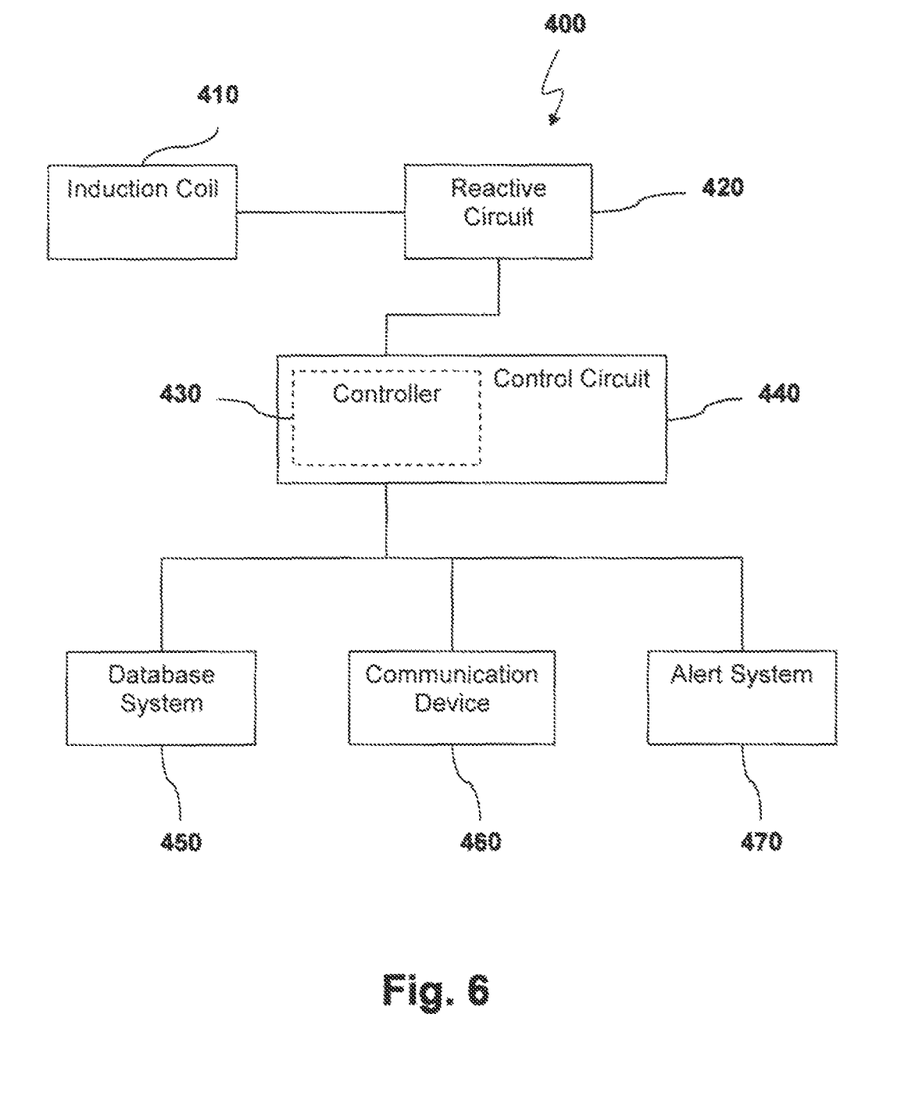
FIG. 6 depicts a block diagram of an exemplary conductivity sensor according to another exemplary embodiment of the present invention.

Referring now to FIG. 6 a block diagram of an exemplary conductivity sensor 400 is disclosed. As illustrated, exemplary conductivity sensor 400 includes an induction coil 410 that may or may not be part of a reactive circuit 420, a control circuit 440 with controller 430, a database system 450, a communication device 460, and an alert system 470.

The control circuit 440 and the controller 430 form the central processing and control circuitry of exemplary conductivity sensor 400. The control circuit 440 may include various devices for maintaining the reactive circuit at resonance when the induction coil is placed adjacent to the specimen. The controller 430 is the main processing unit of the conductivity sensor 400. The controller 430 may be configured to direct the conductivity sensor to perform a plurality of conductivity measurements at predetermined regular or irregular intervals over a period of time. In this manner, the conductivity sensor 400 may be used to perform a series of conductivity measurements of a specimen over a period of time to determine transient effects of the conductivity of the specimen. This type of conductivity sensor is particularly useful for monitoring vascular health of an individual.

Referring still to FIG. 6, conductivity sensor 400 may include a database system 450 operatively connected to controller 430. The database system 450 may be configured to store conductivity measurements made by the conductivity sensor for future use and analysis. For example, the conductivity sensor 400 may be directed by controller 430 to perform a series of conductivity measurements over a time period of three hours at a rate of one conductivity measurement per second. As another example, the conductivity sensor 400 may be directed by controller 430 to perform a series of conductivity measurements over a period of 60 seconds at a rate of 1 conductivity measurement every 10 ms. Those of ordinary skill in the art, using the teachings disclosed herein, will understand that the present invention is not limited to any particular time period or time intervals between conductivity measurements. The database system 450 will store each of the conductivity measurements performed during the time period so that the conductivity measurements can be later analyzed to determine transient effects.

Referring still to FIG. 6, conductivity sensor 400 may include a communication device 460 operably connected to the controller 430. The controller 430 may interact with communication device 460 to interface with various remote devices, such as remote laptop computers. For example, the controller may interact via a Bluetooth® wireless communication module to interface data collection and control application with a remote computer. The Bluetooth® wireless communication interface may be a Bluegiga WT12 Bluetooth® module that allows full duplex serial communications between the remote device and the controller 430. The controller 430 may also communicate via one or more communications networks. It should be appreciated that the communications device or medium can include one or more networks of various forms. For example, a network can include a dial-in network, a local area network (LAN), wide area network (WAN), public switched telephone network (PSTN), the Internet, intranet or other type(s) of networks. A network may include any number and/or combination of hard-wired, wireless, or other communication links.

Still referring to FIG. 6, the controller 430 may be operably connected to alert system 470. Alert system 470 may be configured to provide a visual or audible alarm when the conductivity of a specimen reaches a certain threshold. For example, in a particular embodiment, the alert system 470 could be configured to light up an LED device when the conductivity of the specimen reaches a certain threshold. In another embodiment, the alert system 470 could be configured to sound an audible alarm when the conductivity of the specimen reaches a certain threshold. In still another embodiment, the alert system 470 could provide notification to remote personnel through communication device 460 when the conductivity of the individual reaches a certain threshold.

Figure 7A:
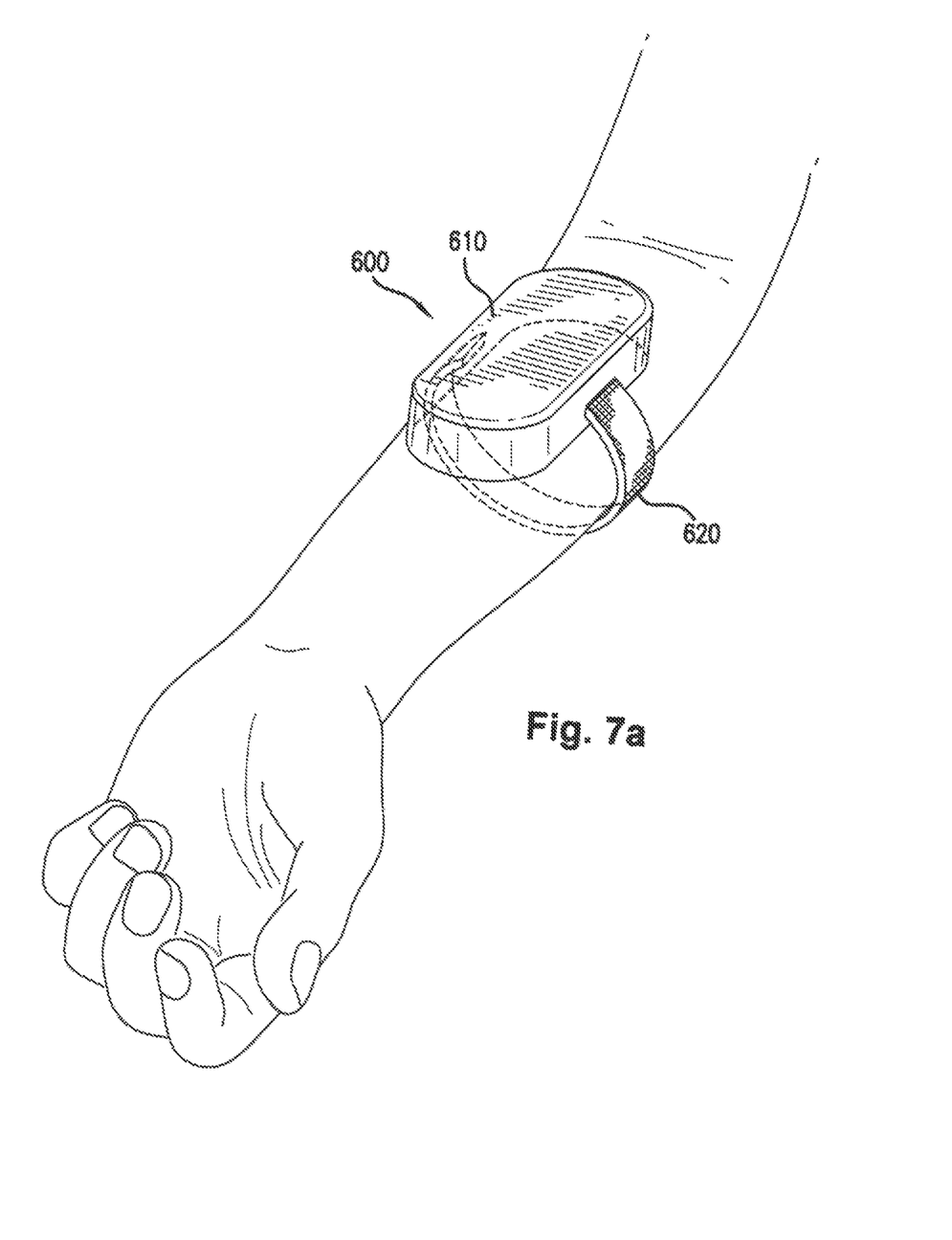
FIG. 7a depicts an exemplary conductivity sensor adapted to be maintained adjacent to an extremity of an individual according to one embodiment of the present invention.
Figure 7B:
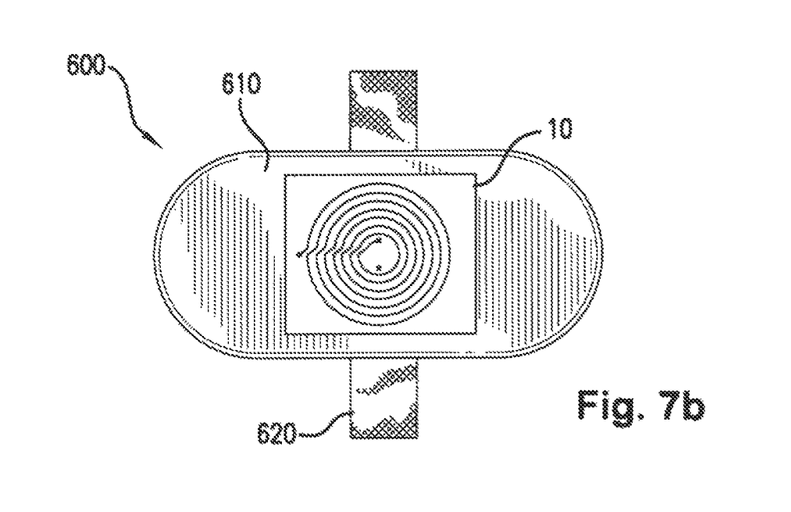

Conductivity sensors according to the present technology may be packaged in a variety of forms, depending on the intended application of the conductivity sensor. For instance, as illustrated in FIGS. 7a and 7b, conductivity sensor 600 may be packaged into a compact housing 610. As used herein, the term "compact housing" refers to any housing that has a length of less than about 25 cm, such as less than about 15 cm, such as less than about 10 cm. Compact housing 610 stores all necessary electronics and circuitry for operation of the conductivity sensor 600, including any database for storage of conductivity measurement data, communications device for interfacing with remote devices, and alert systems for providing an alert if the conductivity measurement reaches a certain threshold.

The compact conductivity sensor 600 illustrated in FIG. 7*a* may be maintained adjacent to an individual using any structure or materials for affixing or securing the conductivity sensor 600 to the individual. For example, as illustrated in FIG. 7*a*, conductivity sensor 600 may include a strap 620 that is used to secure the conductivity sensor to the arm of the individual. In another embodiment, the conductivity sensor 600 may be maintained adjacent to the individual by use of an adhesive material. Such adhesive material may include medical grade skin adhesives such as 3M Double Coated Spunlace Nonwoven Tape 9917 manufactured by the 3M Company and/or 3M Transfer Adhesive1524 manufactured by the 3M Company. By maintaining the conductivity sensor 600 adjacent to the individual, the conductivity sensor may perform a series of conductivity measurements on the specimen for a period of time. The conductivity sensor 600 may be particularly useful for continuously monitoring the conductivity of the extremity of an individual to determine transient effects of the conductivity of the individual.

FIG. 7*b* depicts a plan view of the conductivity sensor 600 illustrated in FIG. 7*a*. As shown, conductivity sensor 600 includes an induction coil 10 similar to induction coil 10 illustrated in FIG. 1*b* and FIG. 1*c*. The housing 610 and strap 620 are used to continuously maintain the induction coil 10 adjacent to the specimen to continuously monitor the conductivity of the specimen.

In another exemplary embodiment of the present invention, the conductivity sensor is used as part of a medical sling for elevating an extremity of the individual. The sling may comprise a conductivity sensor similar to that shown in FIG. 6 for continuously monitoring the conductivity of the extremity. If the conductivity of the extremity reaches a certain threshold caused for example by a drop in blood circulation in the extremity, the conductivity sensor may be adapted to provide an indication or alert indicating that the conductivity of the extremity has reached a certain threshold.

In another exemplary embodiment of the present invention, the conductivity sensor may be incorporated into a garment or uniform. Such a conductivity sensor would be particularly useful in combat scenarios, law enforcement scenarios, or other scenarios where individuals may be placed in danger of harm resulting in the loss of blood. The uniform or garment may comprise a conductivity sensor similar to that shown in FIG. 6 for continuously monitoring the conductivity of the extremity. If the conductivity of the individual wearing the garment or uniform reaches a certain threshold, the conductivity sensor may send an alert to medical personnel warning that a person may be about to enter into circulatory shock.

Figure 8:
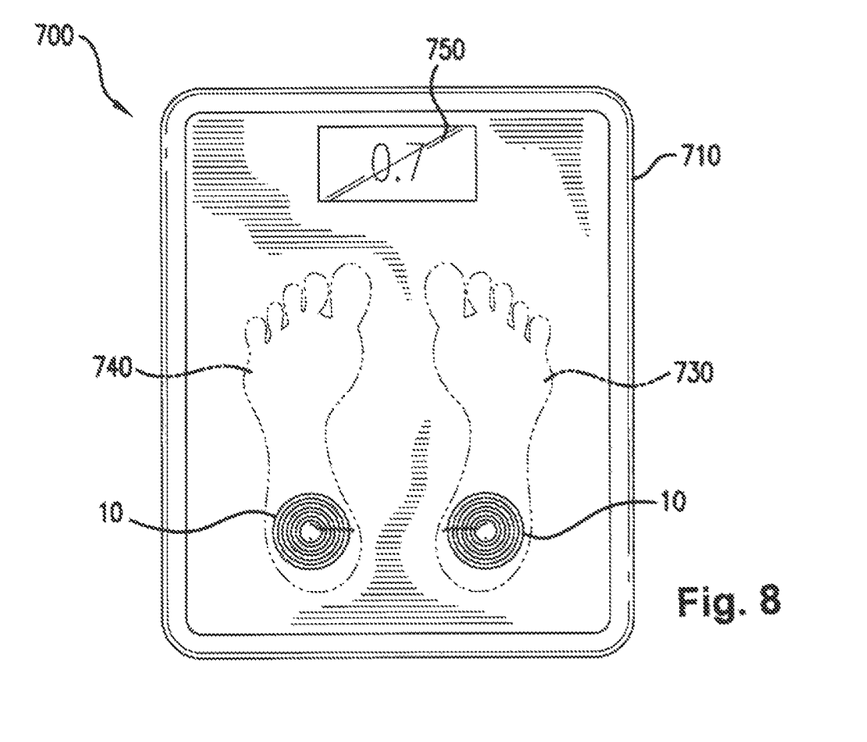
FIG. 8 depicts an exemplary platform unit according to one exemplary embodiment of the present invention.

Referring now to FIG. 8, a platform unit 700 for measuring the conductivity of an individual is disclosed. The platform unit includes a base unit 710 configured to support an individual standing on the platform unit 700. The base unit 710 may enclose all of the necessary electronics and circuitry for operation of the platform unit 700, including any database for storage of conductivity measurement data, communications device for interfacing with remote devices, and alert systems for providing an alert if the conductivity measurement reaches a certain threshold.

As illustrated, the platform unit 700 includes two areas 730 and 740 for receiving a person's feet standing on the platform unit 700. Located within the areas 730 and 740 are induction coils 10. Induction coils 10 may be similar to induction coil 10 illustrated in FIG. 1*b* and FIG. 1*c*. When a person stands on the platform unit 700, induction coils 10 perform a conductivity measurement of the person's feet. The conductivity measurement is displayed to the individual through visual display 750. In particular embodiments, the conductivity measurements may be stored in a database, communicated to a remote device, or used to trigger an alarm if the conductivity measurement is at or beyond a certain threshold.

The platform unit 700 allows an individual to periodically perform conductivity measurements using a simple device that is similar to a typical scale found in a person's home. An individual with vascular health issues could use platform unit 700 to periodically monitor the individual's vascular health from the convenience of the individual's home.

The conductivity sensor of the present invention can perform conductivity measurements on a variety of specimens and for a variety of applications, including the monitoring of an individual's vascular health. Using the teachings disclosed herein, those of ordinary skill in the art should readily appreciate that particular applications of the conductivity sensor are not meant as limitations of the present invention.

While the present subject matter has been described in detail with respect to specific exemplary embodiments and methods thereof, it will be appreciated that those skilled in the art, upon attaining an understanding of the foregoing may readily produce alterations to, variations of, and equivalents to such embodiments. Accordingly, the scope of the present invention is by way of example rather than by way of limitation, and the subject invention does not preclude inclusion of such modifications, variations and/or additions to the present subject matter as would be readily apparent to one of ordinary skill in the art.

What is claimed is:

1. A conductivity sensor comprising:
   a circuit board comprising a first side and an opposing second side; and
   an induction coil adapted to be placed adjacent to a specimen, the induction coil comprising:
   a first conductive element that spirals outward on the first side of the circuit board to an external perimeter from a first terminal located inward of the external perimeter; and
   a second conductive element operably electrically connected to the first conductive element at the external perimeter, the second conductive element spiraling inward on the opposing second side of the circuit board from the external perimeter staggered relative to the first conductive element to a second terminal located inward of the external perimeter, wherein the first conductive element passes through to the second side of the circuit board at the external perimeter so as to electrically connect to the second conductive element at the external perimeter.

2. The induction coil of claim 1, wherein the first conductive element spirals outward to an external diameter, the external diameter being in the range of about 5 mm to 120 mm.

3. The conductivity sensor of claim 1, wherein the induction coil comprises a circular shape, elongated shape, elliptical shape, rectangular shape, triangular shape, hemispherical shape, or fructo-hemispherical shape.

4. The conductivity sensor of claim 1, wherein the induction coil comprises a surface adapted to match the contours of the specimen.

5. The conductivity sensor of claim 4, wherein the surface of the induction coil is a concave surface, convex surface, or waved surface.

6. The conductivity sensor of claim 1, wherein the induction coil comprises a protective coating.

7. The conductivity sensor of claim 6, wherein the protective coating comprises an insulating polymer.

8. The conductivity sensor of claim 6, wherein the protective coating has a thickness in the range of about 0.05 mm to about 1.2 mm.

9. The conductivity sensor of claim 1, wherein the conductivity sensor comprises:
- a base unit; and
- a modular induction coil cartridge adapted to engage the base unit;
- wherein the modular induction coil cartridge is removable so that a variety of different modular induction coil cartridges may be used with the base unit.

\* \* \* \* \*